United States Patent [19]

Solar

[11] Patent Number: 4,546,759
[45] Date of Patent: Oct. 15, 1985

[54] METHOD AND APPARATUS FOR ASSISTING HUMAN HEART FUNCTION

[76] Inventor: Mladen Solar, 116-79th St., Brooklyn, N.Y. 11209

[21] Appl. No.: 518,387

[22] Filed: Jul. 29, 1983

[51] Int. Cl.$^4$ ............................................. A61B 19/00
[52] U.S. Cl. .................................... 128/1 D; 604/101
[58] Field of Search .......... 128/1 D, 325, 344, 207.15; 604/96–103, 4–10

[56] References Cited

U.S. PATENT DOCUMENTS

| | | |
|---|---|---|
| 3,504,662 | 4/1970 | Jones . |
| 3,692,018 | 9/1972 | Goetz et al. ........................ 128/344 |
| 3,877,838 | 4/1975 | Choy . |
| 4,040,413 | 8/1977 | Ohshiro ............................. 604/101 |
| 4,261,339 | 4/1981 | Hanson et al. . |
| 4,276,874 | 7/1981 | Wolvek et al. . |
| 4,423,725 | 1/1984 | Baran et al. ........................ 604/101 |

Primary Examiner—C. Fred Rosenbaum
Assistant Examiner—Mario Costantino
Attorney, Agent, or Firm—Brumbaugh, Graves, Donohue & Raymond

[57] ABSTRACT

A method and apparatus for assisting right ventricle function of the human heart is described. A catheter having three longitudinally spaced balloon elements is inserted into the blood vessels adjacent the heart such that the first and third balloon elements are disposed in the superior vena cava and the inferior vena cava, respectively, and the intermediate balloon element in the right atrial chamber. The superior vena cava and the inferior vena cava are simultaneously occluded by inflation of the first and third balloon elements and, after occlusion, the atrial chamber is pressurized, by inflation of the intermediate balloon element, to urge blood flow through the tricuspid valve into the right ventricle. The first and third balloon elements are then deflated to allow blood flow to resume through the respective vessels and, thereafter, the intermediate balloon element is deflated to allow the atrial chamber to fill with blood. The cycle is repeated periodically at the heart rate. Control of inflation and deflation of the balloon elements is effected by separate gas supply and exhaust means coupled through a dual lumen catheter tube to the balloon elements and actuated in timed sequence.

10 Claims, 2 Drawing Figures

METHOD AND APPARATUS FOR ASSISTING HUMAN HEART FUNCTION

BACKGROUND OF THE INVENTION

This invention relates to a method and apparatus for assisting the function of the human heart and, more particularly, to a method and apparatus for assisting the function of the right ventricle of the human heart.

It is known in cases of human heart disease to aid the function of the left ventricle of the heart, which supplies blood through the aortic artery to the circulatory system, by means such as a balloon catheter. Such catheters consist of a long, flexible hollow tube carrying an inflatable balloon at one end, which is inserted, generally through the femoral artery, into the aorta. By periodically inflating and deflating the balloon, in time with the normal heart rhythm, pressure in the arterial system is maintained at or near normal value, lessening strain on the left ventricle and allowing healing of any injury to that chamber of the heart. Catheter devices of this type are illustrated in U.S. Pat. Nos. 4,261,339 and 4,276,874, for example.

Where injury or defect in the right ventricle of the heart occurs, it is more difficult to assist its function, such as with a balloon catheter, because of the arrangement of the connecting blood vessels.

SUMMARY OF THE INVENTION

The difficulty in providing assistance to right ventricle function is overcome by the method and apparatus of the invention. It has been found that, by pressurizing the right atrial chamber at the proper time in the heart cycle, the ability of the right ventricle to provide blood to the pulmonary artery is considerably abetted and proper heart function achieved even when the right ventricle has suffered an infarct or is otherwise not operating properly. To permit this pressurization to urge blood from the right atrium into the right ventricle, major blood vessels communicating with the atrial chamber, i.e., the superior vena cava and the inferior vena cava, are closed off, leaving the only path for the pressurized blood from the atrial chamber to be through the tricuspid valve to the right ventricle.

In accordance with the invention, the superior and inferior vena cavae first are simultaneously occluded and shortly thereafter the atrial chamber is pressurized to urge the blood into the ventricle. After the ventricle is filled with blood, the occlusions in the associated blood vessels are removed, allowing free blood flow to resume and, finally, the pressurization of the atrium is relieved, allowing it to refill with blood. This sequence of occlusion, pressurization, unblocking and depressurization occurs periodically at the heart rate. Preferably, pressurization of the atrial chamber occurs at right ventricle diastole, i.e., when the right ventricle is relaxed.

The novel apparatus for performing the above sequence of operations comprises a dual lumen catheter having three longitudinally spaced balloon elements. The first and third balloon elements are coupled, for inflation and deflation, with one of the lumens and the intermediate balloon is coupled to the other of the two lumens. Separate means for supplying and exhausting an inflation medium, e.g., air or other gas, are connected individually to the two lumens and the two supply and exhaust means are actuated in timed relation by appropriate control means.

BRIEF DESCRIPTION OF THE DRAWINGS

The foregoing and other objects, features and advantages of the invention will become more apparent from the following detailed description thereof, when taken in conjunction with the appended drawings, in which.

DETAILED DESCRIPTION OF THE INVENTION

Figure 1:
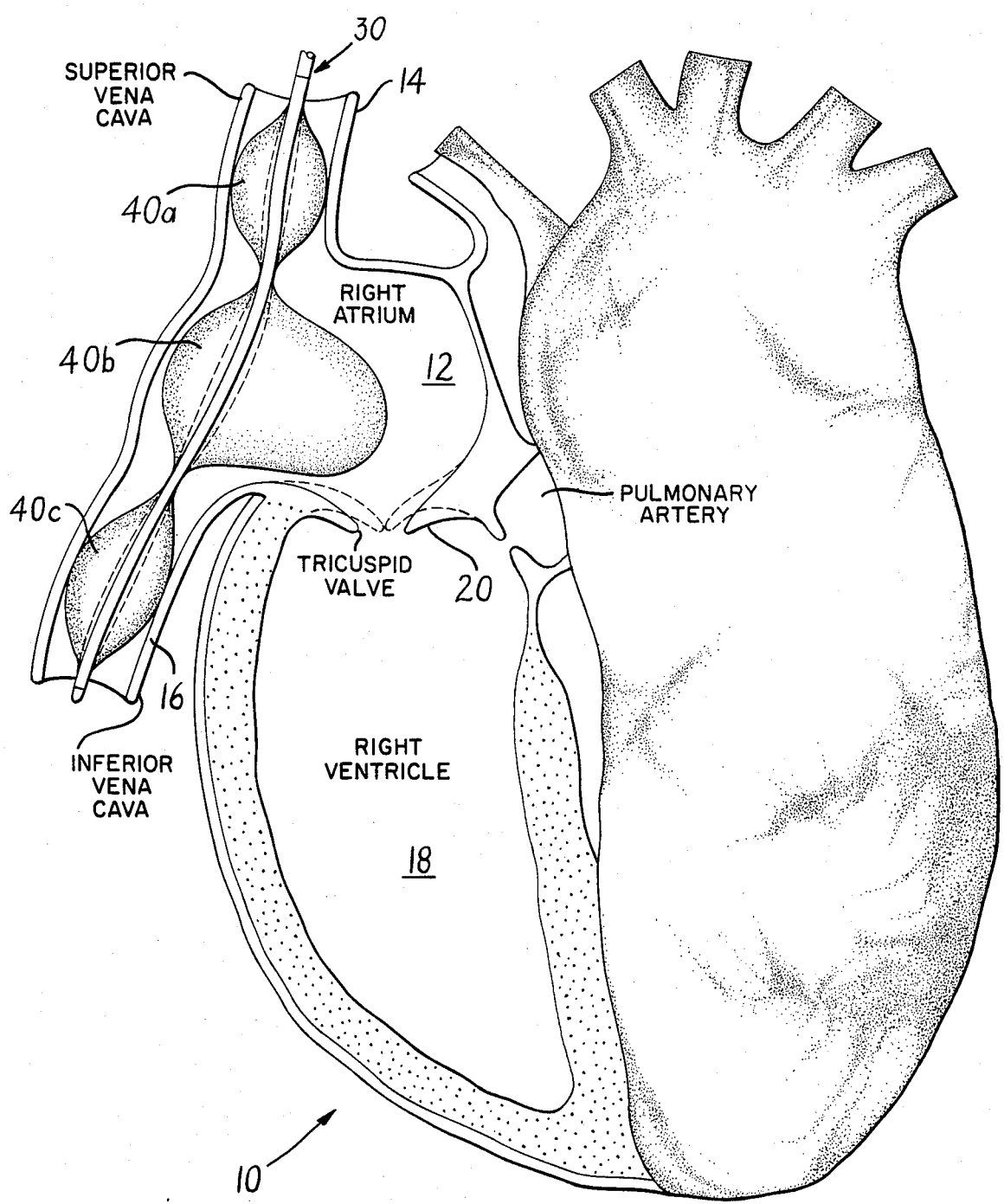
FIG. 1 is a schematic representation of the human heart, partially cut away, with the catheter of the invention in place.

In the simplified illustration of the human heart of FIG. 1, the principal elements of the right side of the heart 10 are shown. In normal operation, blood returning from the circulatory system of the body enters the right atrium or atrial chamber 12 via the superior vena cava 14 and the inferior vena cava 16. With the right ventricle 18 relaxed (diastole) the tricuspid valve 20 is open (solid line) and the blood fills the right ventricle. Upon contraction of the right ventricle (systole) the tricuspid valve closes (dotted line) and the blood is pumped into the pulmonary artery and into the lungs.

As seen in FIG. 1, occlusion of the blood vessels 14,16 adjacent the right atrium is accomplished by means of balloon elements 40a and 40c on a catheter 30 which extends downwardly through the superior vena cava, the atrial chamber and into the inferior vena cava. The balloon elements 40a,40c are spaced such that they will be disposed in the respective vena cava upon insertion. The intermediate balloon element 40b is spaced with respect to the elements 40a and 40c such that it is disposed in the right atrium. After balloon elements 40a and 40c are inflated to occlude their respective blood vessels, the intermediate balloon element 40b is inflated to pressurize the blood in the right atrium and force it into the right ventricle. After the right ventricle is filled, balloon elements 40a and 40c are deflated, permitting blood flow into the right atrium to resume and, finally, the intermediate balloon element 40b is deflated.

The above cycle of operation is repeated at the desired normal heart rate for as long as is necessary to enable the right ventricle to resume its independent operation.

Figure 2:
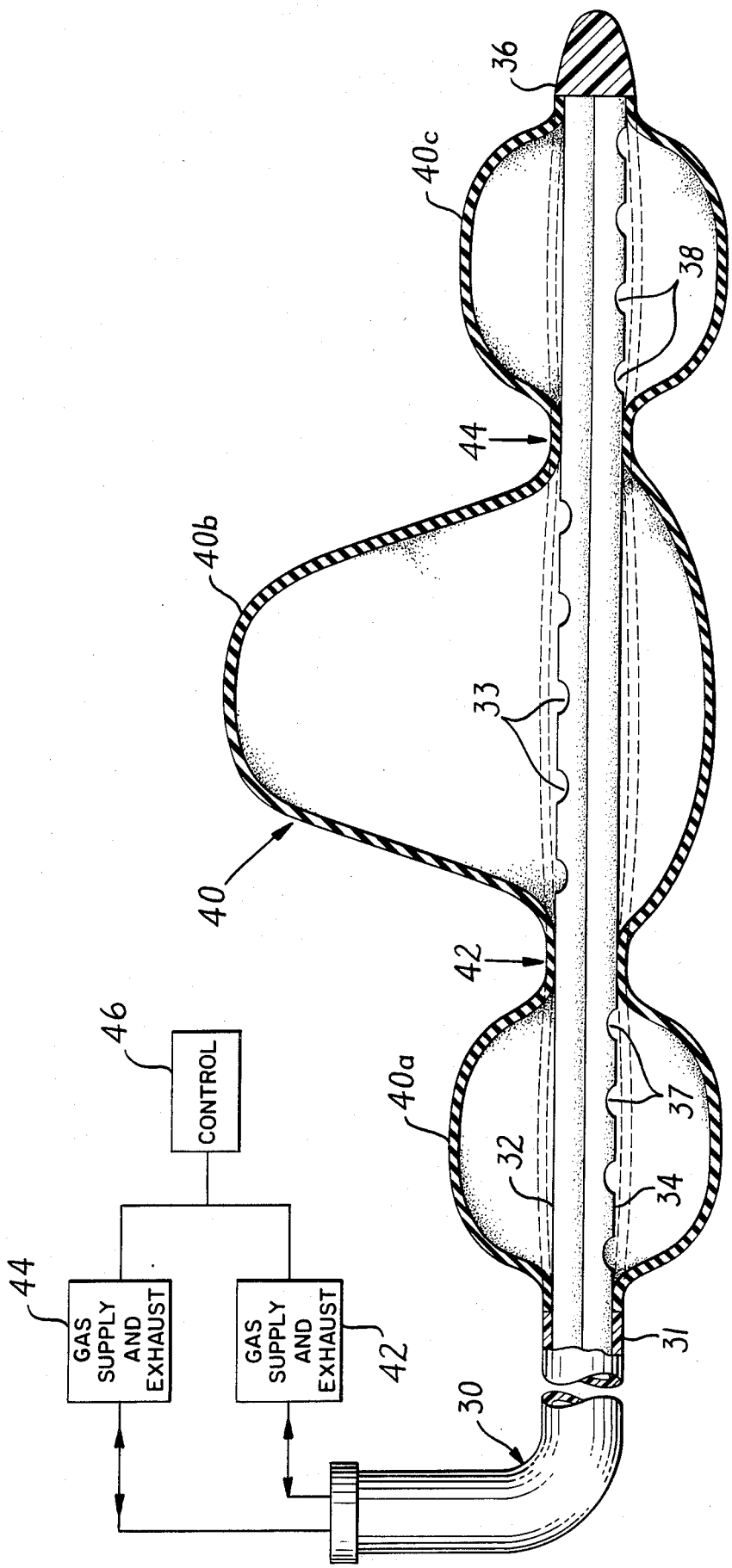
FIG. 2 illustrates, partially in cross-section, the catheter structure of the invention.

A catheter structure according to the invention is illustrated in FIG. 2. The catheter tube 30 includes dual lumens 32,34 and is terminated at its distal end by a rounded tip 36 which facilitates threading of the catheter through the blood vessels into place. The sheath 31 of the catheter, as well as the lumens 32 and 34, preferably are formed of a flexible plastic material to enable the catheter readily to follow the curving path of the blood vessels through which it is threaded. Although not shown in the drawing, a central stiffening wire may be provided centrally of the catheter tube to facilitate insertion and withdrawal.

The dual lumens 32,34 are shown in FIG. 2 as side-by-side tubes but any arrangement for providing separate paths to the balloon elements, as described hereinafter, may be employed.

Surrounding the end of the catheter adjacent the tip 36 is a balloon 40, formed of a thin, flexible material, which may or may not be elastic as desired. In the embodiment illustrated, a single balloon is shown, joined circumferentially around the lumens at 42 and 44 in gastight relationship therewith so as to form three separate balloon elements 40a, 40b and 40c. Lumen 32 is coupled to balloon element 40b by means of holes 33 in the lumen which allow supply and withdrawal of the inflating medium, such as a gas, to the balloon element. Similarly, lumen 34 is coupled to balloon element 40a by holes 37 and to balloon element 40c by holes 38. It will be seen that balloon elements 40a and 40c, both being coupled to lumen 34, will be inflated and deflated simultaneously. The solid lines indicate the balloon elements in their inflated condition; the dotted lines when deflated. Preferably, the element 40b is asymmetrical to conform more nearly to the shape of the atrial chamber.

Inflation and deflation of the balloon elements may be accomplished by any suitable gas supply and exhaust means. Such means comprises two individual gas supply and exhaust systems 42,44, coupled to lumens 32 and 34, respectively, and cyclically actuated in the desired time sequence by the control means 46. Typically, the supply and withdrawal means 42,44 include a gas source and a valve, the latter capable of switching the gas supply to the outlet tube in one position and, in the other position, closing off the gas supply and venting the tube to atmospheric pressure. The control mcans 46 may comprise electro-mechanical or electronic means for periodically opening and closing the valves in the supply means 42 and 44 in desired sequence and frequency.

It will be understood that various modifications of the described invention will occur to those skilled in the art and it is intended that the scope of the invention be limited only by the appended claims.

I claim:

1. A method of assisting right ventricle function of the human heart comprising the steps of
   simultaneously occluding both the superior and inferior vena cava blood vessels,
   while said vessels are occluded, pressurizing the atrial chamber communicating with the right ventricle to urge blood flow through the tricuspid valve,
   thereafter opening said vessels to permit blood flow therethrough, and
   after blood flow through said vessels has resumed, depressurizing the atrial chamber to enable blood to enter said chamber.

2. The method of claim 1 wherein the series of steps is cyclically repeated at the periodicity of the heart.

3. The method of claim 2 wherein during each cycle, pressurization of the atrial chamber occurs during right ventricle diastole.

4. A method of assisting the function of the right ventricle of the human heart comprising the steps of
   inserting a balloon catheter having three balloon elements such that a separate balloon element is disposed in each of the superior vena cava, the atrial chamber and the inferior vena cava, respectively,
   inflating the balloon elements in the superior vena cava and the inferior vena cava simultaneously to occlude both said blood vessels,
   while said vessels are occluded, inflating the balloon element in the atrial chamber to pressurize said chamber to urge blood flow through the tricuspid valve,
   thereafter deflating the balloon elements in the superior vena cava and the inferior vena cava to permit blood flow therethrough, and
   after resumption of blood flow through said vessels, deflating the balloon element in the atrial chamber to allow blood to enter said chamber.

5. The method of claim 4 wherein the series of steps is cyclically repeated at the periodicity of the heart.

6. The method of claim 5 wherein during each cycle, inflation of the balloon element in the atrial chamber occurs during right ventricle diastole.

7. An intra-vascular pressurizing apparatus comprising
   a dual lumen catheter tube,
   three balloon elements mounted on said catheter tube, in longitudinally spaced apart relation, each of said ballon elements capable of being inflated and deflated,
   the intermediate balloon element being asymmetrical with respect to said catheter tube when inflated,
   means coupling one of the lumens of said catheter tube with the first and third of said balloon elements for supplying an inflating medium to and withdrawing said medium from both said first and third balloon elements simulaneously,
   means coupling the other of said lumens to said intermediate balloon element for supplying an inflating medium to and withdrawing said medium from said intermediate balloon element,
   individual means for supplying and withdrawing an inflating medium coupled to each of said lumens, respectively, and
   means for controlling the operation of said supplying and withdrawing means in a predetermined sequence.

8. Catheter apparatus comprising:
   a dual lumen catheter tube,
   three balloon means mounted on said catheter tube, each of said balloon means capable of being inflated and deflated, said balloon means being longitudinally spaced apart from each other on said catheter tube such that when said catheter tube is inserted into position adjacent the human heart, the first of said balloon means is disposed in the inferior vena cava, the third of said balloon means is disposed in the superior vena cava, and the intermediate balloon means is disposed in the right atrial chamber,
   means coupling one of the lumens of said catheter tube with said first and third balloon means for supplying an inflating medium to and withdrawing said medium from both said first and third balloon means to occlude the inferior vena cava and the superior vena cava respectively,
   means coupling the other of said lumens to said intermediate balloon means for supplying an inflating medium to and withdrawing said medium from said intermediate balloon means to aid in pressurinzing the right atrial chamber,
   individual means for supplying and withdrawing an inflating medium coupled to each of said lumens, respectively, and
   means for controlling the operation of said supplying and withdrawing means in a predetermined sequence.

9. The catheter apparatus of claim 8, wherein said balloon means are sized such that, when said catheter is inserted and said balloon means are inflated, said first ballon means occludes the inferior vena cava, said third balloon means occludes the superior vena cave and said intermediate balloon means protrudes into the right artial chamber and pressurizes the chamber to urge blood flow through the tricuspid valve.

10. The catheter apparatus of claim 9, wherein said intermediate balloon means is asymmetrical with respect to said catheter tube when inflated.

* * * * *

UNITED STATES PATENT AND TRADEMARK OFFICE
CERTIFICATE OF CORRECTION

PATENT NO. : 4,546,759

DATED : Oct. 15, 1985

INVENTOR(S) : Mladen Solar

It is certified that error appears in the above-identified patent and that said Letters Patent is hereby corrected as shown below:

Col. 4, line 45, after "means" insert --simultaneously--, and line 50, "pressurinzing" should read --pressurizing--.

Signed and Sealed this

Fourth Day of February 1986

[SEAL]

Attest:

Attesting Officer

DONALD J. QUIGG

Commissioner of Patents and Trademarks